(12) United States Patent
Limousin

(10) Patent No.: US 6,181,968 B1
(45) Date of Patent: Jan. 30, 2001

(54) ACTIVE IMPLANTABLE MEDICAL DEVICE OF THE MULTISITE TYPE

(75) Inventor: Marcel Limousin, Paris (FR)

(73) Assignee: Ela Medical S.A., Montrouge (FR)

( * ) Notice: Under 35 U.S.C. 154(b), the term of this patent shall be extended for 0 days.

(21) Appl. No.: 09/247,573

(22) Filed: Feb. 11, 1999

(30) Foreign Application Priority Data

Feb. 13, 1998 (FR) .................................................. 98 01788

(51) Int. Cl.⁷ ...................................................... A61N 1/37
(52) U.S. Cl. ............................................................ 607/28
(58) Field of Search ................................. 607/4, 5, 9, 24, 607/28

(56) References Cited

U.S. PATENT DOCUMENTS

| | | | |
|---|---|---|---|
| 5,411,533 | 5/1995 | Dubreuil et al. | 607/28 |
| 5,564,430 | 10/1996 | Jacobson et al. | 128/697 |
| 5,601,615 | * 2/1997 | Markowitz et al. | 607/28 |
| 5,800,465 | * 9/1998 | Thompson et al. | 607/9 |
| 5,871,508 | * 2/1999 | Thompson et al. | 607/9 |

FOREIGN PATENT DOCUMENTS

| | | | |
|---|---|---|---|
| 0 479 215 | 4/1992 | (EP) | A61N/1/365 |
| 0 653 225 | 5/1995 | (EP) | A61N/1/37 |
| WO 86/05698 | 10/1986 | (WO) | A61N/1/36 |
| WO 9604956 | 2/1996 | (WO) | A61N/1/365 |

OTHER PUBLICATIONS

J.C. Daubert, et al.; "Quel avenir pour la stimulation comme traitement primaire de l'insuffisance cardiaque?", *Stimuvoeur*, 1997, vol. 25, issue 3, pp. 170–176.

* cited by examiner

Primary Examiner—Jeffrey R. Jastrzab
(74) *Attorney, Agent, or Firm*—Orrick, Herrington & Sutcliffe LLP

(57) ABSTRACT

An active implantable medical device, particularly a pacemaker, defibrillator and/or cardiovertor of the "multi-site" type, in which electrodes are placed in at least two neighboring cardiac sites, e.g., right and left ventricular sites, and/or right and left atrial sites. These electrodes are connected to a cardiac signal sensing circuit to detect a potential of depolarization on the corresponding site(s). These electrodes also are connected to a stimulation circuit to apply, if necessary, a stimulation impulse on the same site(s). The device adjusts the amplitude of stimulation in relation with the capture threshold and a total refractory period comprising an absolute refractory period, in which all detection is inhibited, followed by a relative refractory period. The detection of a depolarization during the relative refractory period marks the absence of a capture. It is advantageously foreseen to adjust the instant of beginning of the relative refractory period, notably by progressive increase of the duration of the relative refractory period over several successive cycles, until there is a detection of a depolarization in this relative refractory period. This indicates a loss of capture and allows for setting the stimulation amplitude above the capture threshold.

18 Claims, 2 Drawing Sheets

ACTIVE IMPLANTABLE MEDICAL DEVICE OF THE MULTISITE TYPE

FIELD OF THE INVENTION

The present invention concerns "active implantable medical devices" such as those devices defined by the Jun. 20, 1990 directive 90/385/EEC of the European Community Council, more particularly devices which are able to deliver to the heart electrical impulses of low energy (stimulation impulses) for the processing of troubles of the cardiac rhythm such as cardiac pacemakers, defibrillators and/or cardiovertors. It more particularly concerns the so-called "multisite" prostheses, that is to say prostheses in which electrodes are placed in a plurality of distinct respective sites on the heart, typically with at least two ventricular sites.

Such a multisite cardiac prosthesis can be of the type known as "double chamber" (double ventricular stimulation), triple chamber (right atrial stimulation and double ventricular stimulation) or quadruple chamber (double atrial stimulation and double ventricular stimulation).

BACKGROUND OF THE INVENTION

It is known to treat troubles of the cardiac rhythm (arrhythmias) with cardiac stimulation. It also has been proposed to treat troubles of the myocardium contraction observed in patients with cardiac insufficiency (hereinafter "troubles") with cardiac stimulation. These latter troubles can originate spontaneously or can be induced by a traditional cardiac stimulation impulse. Reference is made to the study of J. C. Daubert et al., Stimucœur, Volume 25, n°3, pp. 170–176 (1997) which describes the state of the art on this subject. It has already been proposed to stimulate simultaneously the right and left ventricles, which is known as a "double stimulation". This technique also can be applied to a double stimulation of the atria (i.e., the left and right atria).

One of difficulties of the known multisite stimulation is to guarantee the efficiency of the stimulation on the different cardiac sites. In particular, one generally observes different stimulation thresholds between the right site and the left site. This can result in a defective (e.g., insufficient) stimulation or an erroneous depolarization wave detection (i.e., confusion between an electro-stimulated depolarization originating at the one site and an indirectly sensed depolarization having its origin at the neighboring site). The latter is sometimes called a "far-field" detection.

French patent FR 2 680 093 and its corresponding U.S. Pat. No. 5,411,533, commonly owned by the assignee of this invention, describe a device provided with an automatic adjustment of the stimulation impulse amplitude in relation to a determined capture threshold. This adjustment is obtained by a progressive reduction of the stimulation impulse amplitude level over several successive cardiac cycles, detection of the disappearance of the capture, and then reestablishment of the stimulation impulse amplitude at a level slightly greater than the threshold corresponding to the disappearance of capture. The disclosure of U.S. Pat. No. 5,411,533 is incorporated herein by reference.

As is generally understood by persons skilled in the art, "capture" is a cardiac event where there is a depolarization following and responsive to delivery of a stimulation impulse. The "capture threshold" is the minimal voltage level of the stimulation impulse that causes capture, namely the desired depolarization of the cardiac tissue at the stimulation site.

OBJECTS AND SUMMARY OF THE INVENTION

It is an object of the present invention, therefore, to remedy to this difficulty, by providing an automatic adjustment of the of stimulation impulse amplitude of the neighboring sites, e.g., the left site and the right site, in relation with the "capture threshold", that is to say the minimal level of voltage amplitude allowing for a capture on the considered site.

To this end, the invention broadly proposes an active implantable medical device of the aforementioned multisite type, that is to say in which electrodes are respectively placed at least two neighboring cardiac sites. Preferably, the two neighboring cardiac sites are either (1) at least one site in the right ventricle and one site in the left ventricle (also called the "right and left ventricular sites"), or (2) at least one site in the right atrium and one site in the left atrium (also called "the right and left atria sites") or (3) both (1) and (2).

These electrodes are respectively connected to one or more circuits for sensing the cardiac signal in order to detect a depolarization potential on the corresponding site(s), and to one or more stimulation circuits to apply, if necessary, a stimulation impulse on the same site(s). The device also comprises means to determine a capture threshold, and means to adjust the stimulation impulse amplitude in relation to the capture threshold, and means to fix a total refractory period comprising an absolute refractory period during which all detection is inhibited, followed by a relative refractory period.

According to the present invention, the detection of a depolarization during the relative refractory period marks the absence of a capture (also called a "loss of capture").

Very advantageously, it is foreseen to provide a means to adjust the instant of the beginning of the relative refractory period, preferably by a progressive increase of the relative refractory period duration over several successive cardiac cycles, until there is a detection of a depolarization in this relative refractory period, without any modification of the duration of the total refractory period.

Preferably, the duration of the total refractory period is constant and the initial duration of the relative refractory period is null (zero).

It also can be foreseen to provide a means of preliminary detection of the absence of extrasystolic activity, and to condition the implementation of the means for adjusting the stimulation amplitude on the detected absence of extrasystolic activity. The preliminary detection means preferably comprises means to evaluate the maximal time of synchronous depolarization of the two neighboring sites, namely the two ventricular sites and/or the two atrial sites.

Finally, to avoid a false detection, the device advantageously optionally comprises means for detecting a "bigeminy" condition, which is able to inhibit the adjustment of the stimulation impulse threshold, even in case of the detection of a depolarization during the relative refractory period.

BRIEF DESCRIPTION OF THE DRAWINGS

Further features, characteristics and advantages of the present invention will appear to the person of ordinary skill in the art in view of the following detailed description of a preferred, exemplary implementation of the invention, made with reference to the annexed drawings, in which.

DETAILED DESCRIPTION OF THE DRAWINGS

An object of the invention, as indicated above, is to ensure the efficiency of the stimulation of the different sites in a multisite pacing system, by taking into account the fact that one observes, in general, different capture thresholds between the right site and the left site.

The following description refers to right and left ventricular sites (the detection of R waves), but it should be understood that the invention can be applied to the case of two neighboring (left and right) atrial sites, and notably to the case of so called "quadruple chamber" devices including a double ventricular and double atrial stimulation.

Figure 1:
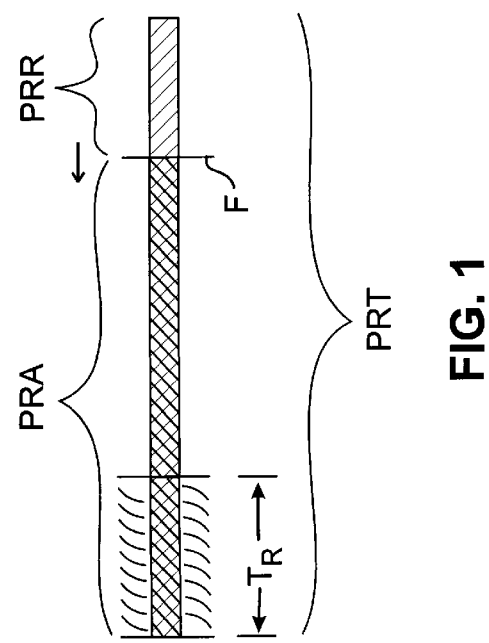
FIG. 1 shows schematically the division of the refractory period in an absolute part and a relative part, with a variable border (F) therebetween.

According to the invention, one divides the total refractory period PRT (the post-ventricular refractory period in the present example hereafter—the post-atrial refractory period in the case of the atria), into two sub-periods, namely an absolute refractory period PRA, followed by a relative refractory period PRR (FIG. 1). The total refractory period PRT is typically a known parameter of the pacemaker, and is generally fixed at a programmed value.

During the absolute refractory period PRA, no signal will be detected, regardless of the nature or the origin of the signal. This absolute refractory period PRA has to be at least equal to the recovery time $T_R$ of the sensing amplifiers, that is typically on the order 50 ms; on the other hand it does not have to be too long, which would risk not detecting possible ventricular extrasystoles, that necessitate the implementation of a particular analysis algorithm.

During the relative refractory period PRR, one will authorize an analysis of the ventricular depolarization for the purpose of the adjustment of stimulation impulse amplitude according to the invention; but a depolarization detected during this relative refractory period PRR will not serve to command delivery of a stimulation impulse (because this period remains a refractory period).

Figure 2:
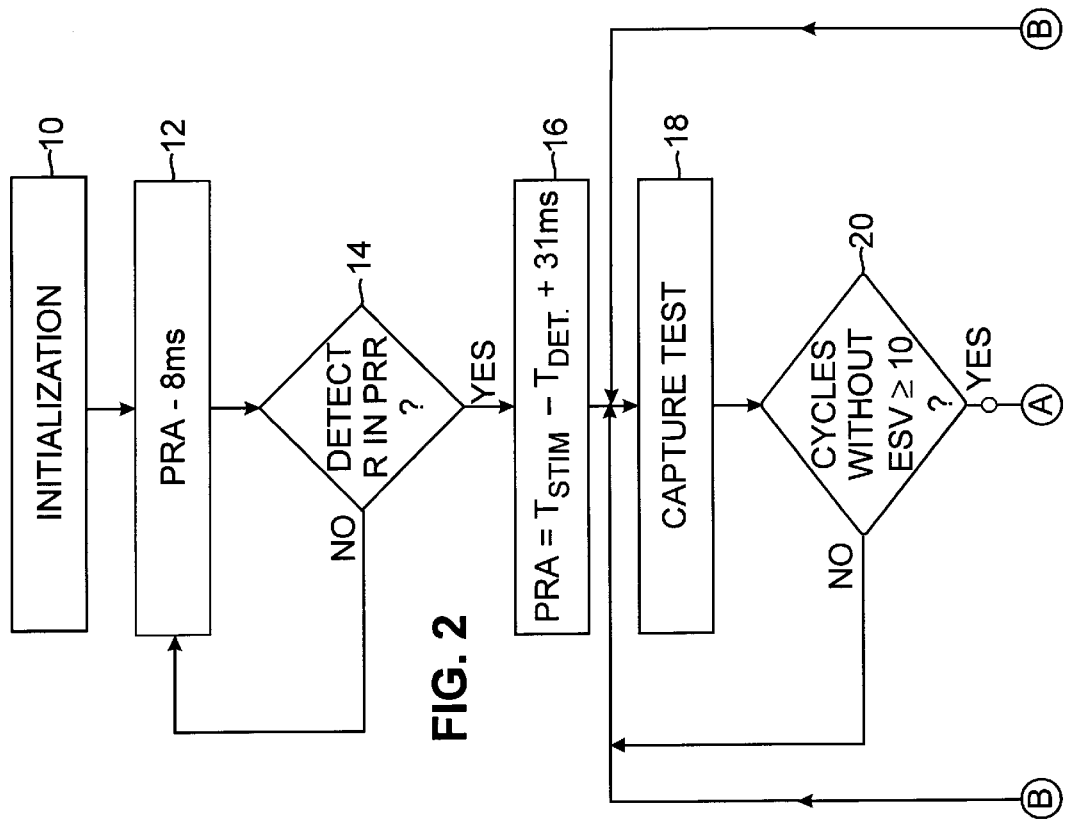
FIGS. 2 and 3 illustrate a flow chart implementating an algorithm for the automatic adjustment of the stimulation amplitude according to the present invention.
Figure 3:
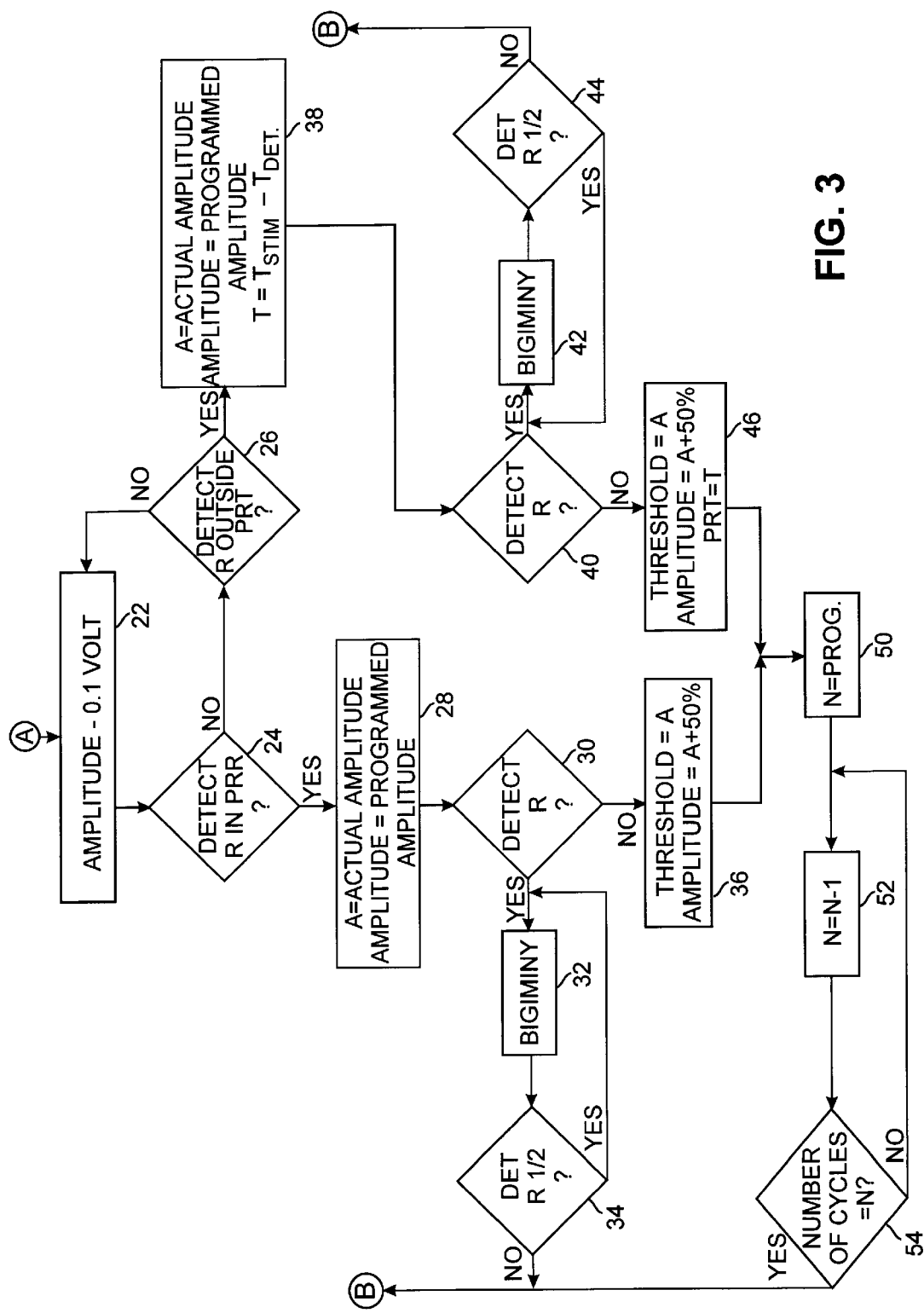

One is going now to describe the progress of the process of adjustment of the stimulation amplitude according to the invention, with reference to flow charts of FIGS. 2 and 3.

During an initialization phase (stage 10), with delivery of a maximal or programmed stimulation impulse energy, the pacemaker initializes the border F between absolute refractory period PRA and relative refractory period PRR to correspond to the initial duration of the total refractory period PRT and gradually displaces the border F to the left (in the direction of the arrow illustrated in FIG. 1) (stages 12 and 14). Typically, the duration of the total refractory period PRT covers the delay of amplifier recovery $T_R$ and the duration of the depolarization, which duration is typically initialized to a value greater than about 150 ms. The change in the border F results in a gradual increase of the relative refractory period PRR of an increment each cycle, e.g., 8 ms.

Furthermore, the multisite capture test is undertaken only if the sinus frequency is between the programmed base frequency and the programmed base frequency increased by 10% (for example), that is to say otherwise the patient is in a rest condition. This precaution, that the patient be at rest before conducting the test, is well known in algorithms of this type.

As soon as a detection appears in the interval of the relative refractory period PRR (stage 14), one memorizes (i.e., determines or measures and/or stores in memory) either (1) the time period T between a stimulation $T_{STIM}$ and the following detection $T_{DET}$ as being the maximal time of synchronous depolarization of the two sites, or (2) the recovery time period of the amplifier $T_R$, if the latter is longer (stage 16). The duration of the absolute refractory period PRA, that is to say in others terms, the position of the border F, is then fixed to a value slightly greater than the time period memorized, for example, an increment of 31 ms. The period corresponding to the difference between the programmed absolute refractory period PRA and the one that is determined in the initialization phase then becomes the relative refractory period PRR.

A second phase of capture research (stage 18) then begins. This phase will begin, however, only if one is sure that the patient has been free of all extrasystolic activity ESV during the last number of cycles, e.g., ten (10) cardiac cycles (stage 20). This is to avoid false detections. In other words, detection of extrasystolic activity during a given duration preceding the request to conduct a capture research will inhibit the redetermination of the stimulation amplitude until the condition of an absence of extrasystolic activity for the given duration (e.g., a number of cycles) is satisfied.

Referring to FIG. 3, if the capture research phase begins, one decreases the stimulation amplitude gradually (stage 22), in an iterative manner, until it is detected that one of the two ventricular sites no longer produces a capture. For this progressive diminution, it is important to be able to have small decrements, for example, of 0.1 V, which decrements are preferably uniform amounts from decrement to decrement.

Thus, in the case of progressively incrementing the relative refractory period from an initial duration of zero, if a ventricular detection R occurs in the relative refractory period PRR, after the absolute refractory period PRA (stage 24), then one has detected the highest threshold of the two cavities. In other words, as long as the capture of the two ventricles is guaranteed, one does not detect anything in the relative refractory period PRR. On the other hand, if a depolarization is detected in the relative refractory period PRR, it is a sign that there has been a loss of capture in one of the two ventricles, and this detection is the sign of a depolarization driven from one ventricle to the other.

Referring again to the example in the Figures, in the following cycle, the pacemaker re-establishes the maximal or the programmed amplitude (stage 28):

a) If an asynchronous R wave detection occurs (stage 30)—that is to say that even if one changes the amplitude of the stimulation impulse, it produces a second depolarization independently of this amplitude, the patient is in "bigeminy" condition (stage 32). A bigeminy condition has alternation between a cycle of normal activity and a cycle of an abnormal activity. It is in this case strongly probable that the detection of the preceding cycle was not linked to the threshold of capture, and one then waits until the end of the stimulation-detection sequence "R ½ "(stage 34) before resuming the test of capture (namely, the procedure returns to stage 18).

b) If no detection occurs in the ventricle (stage 30), then the pacemaker has found the highest capture thresholds of the two cavities, and the pacemaker programs the amplitude of stimulation A to be the threshold found increased by a margin of security, for example, 50% (stage 36).

c) If the detection has occurred out of the relative refractory period (stages 24 and 26), and in the absence of "bigeminy" (stages 38 to 44 are corresponding equivalents of stages 28 to 34), the pacemaker programs the amplitude of stimulation A to the detected threshold plus a margin of security, for example, 50% (stage 46).

Eventually, one can re-program the relative refractory period PRT to a duration T equal to the delay between stimulation and detection ($T_{STIM}-T_{DET}$) plus 31 ms, the relative refractory period PRR being thus lengthened to minimize, if not avoid all risk of, false detection (the stimulation—detection delay T is memorized at stage 38).

The test of capture resumes then, in the same manner as set forth above, after N ventricular stimulation cycles (stages 50, 52, 54), N being a pre-programmed value, chosen to correspond to a duration, for example, of approximately six hours.

One skilled in the art will appreciation that the present invention can be practiced by other than the described embodiments, which are presented for purposes of illustration and not of limitation. For example, it is to be understood that the invention can be implimented in a software routine for a microprocessor controlled active implantable medical device, or in discreet analog and/or digital circuits for such devices. Well known circuits for stimulating cardiac activity, detecting cardiac activity (spontaneous and stimulated) including a capture, and measuring time intervals and processing the same, can be used as a matter of design choice. It also should be understood that the specific time periods described herein are merely exemplary, based on relative values corresponding to the times appropriate for use with desired or of normal cardiac behavior, and also are a matter of design choice.

I claim:

1. An active implantable medical device, particularly a pacemaker, defibrillator and/or cardiovertor of the multisite type, having a capture threshold, in which electrodes are to be placed at at least two neighboring cardiac sites selected from among a right and left ventricular sites, a right and left atrial sites, and a right and left ventricular and atrial sites, these electrodes being connected to a cardiac signal sensing circuit to detect a potential of depolarization on a corresponding site including a capture, and to a stimulation circuit to apply, if necessary, a stimulation impulse on said corresponding site, said device having a capture threshold corresponding to a minimal amplitude level allowing the sensing, on a considered site, of a detected depolarization following a preceding stimulation impulse, comprising:

means for adjusting an amplitude of stimulation in relation to a capture threshold for each cardiac site, said adjusting being responsive to the detection of a capture to adjust said stimulation threshold and the non detection of a capture to fix said threshold; and means for fixing a total refractory period ("PRT") having a duration comprising an absolute refractory period ("PRA") and a relative refractory period ("PRR"), the absolute refractory period corresponding to a time during which all detection is inhibited;

wherein said cardiac signal sensing circuit senses a potential of said at least two neighboring cardiac sites detects a depolarization potential on at least one of said neighboring cardiac sites during the relative refractory period, and determines in response thereto a state of loss of a capture at said at least one cardiac site.

2. The device of claim 1, wherein the relative refractory period comprises an instant (F) of beginning relative to the total refractory period and further comprising means to adjust the instant (F) of the beginning of the relative refractory period.

3. The device of claim 2, further comprising means for operating the means to adjust the instant of the beginning of the relative refractory period by a progressive increase of the duration of said relative refractory period over at least two successive cardiac cycles until there is a detection of a depolarization potential on at least one of said neighboring cardiac sites in said relative refractory period.

4. The device of claim 3, wherein the duration of the total refractory period is constant.

5. The device of claim 3, wherein the initial duration of the relative refractory period is zero.

6. The device of claim 1, further comprising preliminary means for detecting the absence of extrasystolic activity for a given duration, wherein the means for adjusting the stimulation amplitude is controlled in response to said preliminary detection means detecting the absence of extrasystolic activity for the given period.

7. The device of claim 6 wherein the given duration comprises a pre-selected number of cardiac cycles.

8. The device of claim 6, wherein the preliminary means for detecting the absence of extrasystolic activity comprises means for evaluating the maximal time of synchronous depolarization of at least the two neighboring cardiac sites.

9. The device of claim 1, further comprising means for detecting a bigeminy condition, wherein the means for adjusting the stimulation amplitude is inhibited in response to a detected bigeminy condition.

10. A method for controlling a stimulation amplitude in a multisite active implantable device, comprising:

placing an electrode in at least two neighboring cardiac sites selected from among a right and left ventricular site, a right and left atrial site, and a right and left ventricular and atrial site;

providing a capture threshold corresponding to a minimal amplitude level allowing the sensing, on a considered site, of a detected depolarization following a preceding stimulation impulse;

fixing a total refractory period having a duration comprising an absolute refractory period and a relative refractory period, the absolute refractory period corresponding to a time during which all detection is inhibited;

detecting a potential of depolarization on said corresponding sites including a capture;

determining a state of loss of a capture on at least one of said corresponding sites in response to detecting a depolarization during the relative refractory period;

adjusting an amplitude of stimulation in relation to the capture threshold, said adjusting step being responsive to the detection and the loss of a capture at said one corresponding site.

11. The method of claim 10, wherein fixing the total refractory period further comprises initializing a relative refractory period having an instant (F) of beginning relative to the total refractory period, and adjusting the instant (F) of the beginning of the relative refractory period.

12. The method of claim 11, further comprising adjusting the instant of the beginning of the relative refractory period by a progressive increase of the duration of said relative refractory period over at least two successive cardiac cycles until there is a detection of a depolarization in said relative refractory period.

13. The method of claim 12, further comprising fixing the duration of the total refractory period constant.

14. The method of claim 12, further comprising fixing an initial duration of the relative refractory period at zero and progressively increasing the duration of the relative refractory period.

15. The method of claim 10, further comprising detecting the absence of extrasystolic activity for a given duration, and adjusting the stimulation amplitude in response to detecting the absence of extrasystolic activity for said given duration.

16. The method of claim 15, further comprising providing the given duration as a pre-selected number of cardiac cycles.

17. The method of claim 15, wherein detecting the absence of extrasystolic activity further comprises evaluating the maximal time of synchronous depolarization of at least two neighboring cardiac sites.

18. The method of claim 10, further comprising detecting a bigeminy condition and inhibiting the adjustment of stimulation amplitude in response to a detected bigeminy condition.

* * * * *

UNITED STATES PATENT AND TRADEMARK OFFICE
CERTIFICATE OF CORRECTION

PATENT NO. : 6,181,968 B1
DATED : January 30, 2001
INVENTOR(S) : Macel Limousin

It is certified that error appears in the above-identified patent and that said Letters Patent is hereby corrected as shown below:

Column 1,
Line 35, delete "of difficulties" and insert -- of the difficulties -- therefor;
Line 67, delete "remedy to" and insert -- remedy -- therefor;

Column 2,
Line 1, delete "of stimulation" and insert -- stimulation -- therefor;
Line 9, delete "placed at" and insert -- placed in at -- therefor;
Line 52, delete "in case" and insert -- in the case -- therefor;
Line 65, delete "implementating" and insert -- implementing -- therefor;

Column 3,
Line 25, delete "order 50" and insert -- order of 50 -- therefor;

Column 5,
Line 1, delete "appreciation" and insert -- appreciate -- therefor;
Line 21, delete "ventricular sites" and insert -- ventricular site -- therefor;
Line 22, delete "atrial sites" and insert -- atrail site -- therefor;
Line 42, delete "sites" and insert -- sites, -- therefor; and
Line 49, delete "comprising" and insert -- comprises -- therefor.

Signed and Sealed this

Twenty-sixth Day of July, 2005

JON W. DUDAS
*Director of the United States Patent and Trademark Office*